US008734678B2

(12) United States Patent
Marguerettaz et al.

(10) Patent No.: US 8,734,678 B2
(45) Date of Patent: *May 27, 2014

(54) IDENTIFICATION AND AUTHENTICATION USING POLYMERIC LIQUID CRYSTAL MATERIAL MARKINGS

(75) Inventors: Xavier Marguerettaz, Martigny (CH); Frédéric Gremaud, Epagny (CH); Aurélien Commeureuc, Echichens (CH); Vickie Aboutanos, Neuchâtel (CH); Thomas Tiller, Bussigny (CH); Olivier Rozumek, Le Pâquier-Montbarry (CH)

(73) Assignee: SICPA Holding SA, Prilly (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/532,240

(22) Filed: Jun. 25, 2012

(65) Prior Publication Data

US 2013/0069003 A1    Mar. 21, 2013

Related U.S. Application Data

(63) Continuation of application No. 13/262,348, filed as application No. PCT/EP2010/054515 on Apr. 6, 2010, which is a continuation of application No. 12/384,340, filed on Apr. 2, 2009, now abandoned, and a continuation of application No. PCT/EP2009/002434, filed on Apr. 2, 2009.

(51) Int. Cl.
*C09K 19/58* (2006.01)
*C09K 19/54* (2006.01)
*C09K 19/52* (2006.01)
*C09D 11/00* (2014.01)

(52) U.S. Cl.
USPC ............. 252/299.5; 252/299.01; 106/31.13; 106/31.92

(58) Field of Classification Search
USPC .......... 252/299.01, 299.5, 299.67; 106/31.13, 106/31.92
See application file for complete search history.

(56) References Cited

U.S. PATENT DOCUMENTS

| | | | |
|---|---|---|---|
| 5,211,877 A | 5/1993 | Andrejewski et al. |
| 5,360,628 A | 11/1994 | Butland |
| 5,362,315 A | 11/1994 | Muller-Rees et al. |
| 5,502,304 A | 3/1996 | Berson et al. |
| 5,525,798 A | 6/1996 | Berson et al. |
| 5,542,971 A | 8/1996 | Auslander et al. |
| 5,569,317 A | 10/1996 | Sarada et al. |
| 5,611,958 A | 3/1997 | Takeuchi et al. |
| 5,678,863 A | 10/1997 | Knight et al. |
| 5,698,397 A | 12/1997 | Zarling et al. |
| 5,766,324 A | 6/1998 | Ikegaya et al. |
| 5,798,147 A | 8/1998 | Beck et al. |
| 6,114,018 A | 9/2000 | Phillips et al. |
| 6,138,913 A | 10/2000 | Cyr et al. |
| 6,155,605 A | 12/2000 | Bratchley et al. |
| 6,268,058 B1 | 7/2001 | Tahon et al. |
| 6,380,547 B1 | 4/2002 | Gonzalez et al. |
| 6,423,246 B1 | 7/2002 | Kasch et al. |
| 6,472,455 B1 | 10/2002 | Bleikolm et al. |
| 6,545,809 B1 | 4/2003 | Phillips |
| 6,589,445 B2 | 7/2003 | Sugiyama et al. |
| 6,612,494 B1 | 9/2003 | Outwater |
| 6,744,559 B2 | 6/2004 | Phillips |
| 6,751,022 B2 | 6/2004 | Phillips |
| 6,793,720 B2 | 9/2004 | Muller et al. |
| 6,858,323 B1 | 2/2005 | Giering et al. |
| 6,899,824 B2 | 5/2005 | Meyer et al. |
| 7,364,091 B2 | 4/2008 | Streeter |
| 7,441,704 B2 | 10/2008 | Ross |
| 7,599,544 B2 | 10/2009 | Moshe |
| 8,142,682 B2 * | 3/2012 | Kasch et al. ............. 252/299.01 |
| 2003/0056688 A1 | 3/2003 | Muller et al. |
| 2004/0124398 A1 | 7/2004 | Kuntz et al. |
| 2004/0140451 A1 | 7/2004 | Meyer et al. |
| 2006/0147640 A1 | 7/2006 | Kastner et al. |
| 2006/0197791 A1 | 9/2006 | Iriguchi et al. |
| 2007/0224341 A1 | 9/2007 | Kuntz et al. |
| 2008/0036926 A1 | 2/2008 | Chen et al. |
| 2008/0116272 A1 | 5/2008 | Giering et al. |
| 2008/0138543 A1 | 6/2008 | Hoshino et al. |

(Continued)

FOREIGN PATENT DOCUMENTS

| | | |
|---|---|---|
| CN | 101088113 A | 12/2007 |
| DE | 044 18 490 | 11/1995 |

(Continued)

OTHER PUBLICATIONS

Search report and Written Opinion from International Application No. PCT/EP2010/054515, mail date Nov. 5, 2011.
Rudolf L. van Renesse, "Optical Document Security," 2nd Edition, 1998, Chapters 10, pp. 225-247, 13, and 14, pp. 289-347.
J.L. Fergason, "Cholesteric Structure—I Optical Properties," Molecular Crystals, vol. 1, pp. 293-307 (1966).
Bob Williams, "Understanding Barcoding", 2004, Pira International, Ltd.[Cover/Title page, 2pp. and Table of Contents pp. iii-xvii, only] 2004 (ISBN 1 85802 917 1).
Supplementary Search report from International Application No. PCT/EP2010/054515, Aug. 4, 2011.

(Continued)

*Primary Examiner* — Shean C Wu
(74) *Attorney, Agent, or Firm* — Greenblum & Bernstein, P.L.C.

(57) ABSTRACT

The present invention relates to a marking of polymeric liquid crystal material having determined optical characteristics allowing its authentication and reading by a machine and its authentication by the human eye. The marking is applied onto an item, good or article by a variable information printing process. The marking is in the form of indicia representing a unique code which allows for an easy authentication by the human eye and a secure tracking and tracing of the marked item, good or article throughout is life cycle.

31 Claims, 2 Drawing Sheets

(56) References Cited

U.S. PATENT DOCUMENTS

| | | |
|---|---|---|
| 2008/0294900 A1 | 11/2008 | Cowburn |
| 2010/0038598 A1 | 2/2010 | Bastiaansen et al. |
| 2010/0104826 A1 | 4/2010 | Bastiaansen et al. |
| 2010/0178508 A1* | 7/2010 | Kasch et al. ............... 428/402 |
| 2010/0200649 A1 | 8/2010 | Callegari et al. |
| 2011/0101088 A1 | 5/2011 | Marguerettaz et al. |
| 2012/0061470 A1 | 3/2012 | Marguerettaz et al. |
| 2012/0273722 A1* | 11/2012 | Marguerettaz et al. .... 252/299.5 |

FOREIGN PATENT DOCUMENTS

| | | |
|---|---|---|
| DE | 199 22 158 | 11/2000 |
| DE | 102 07 180 | 2/2002 |
| DE | 102 11 310 | 10/2003 |
| EP | 0 216 712 A | 4/1987 |
| EP | 0 601 483 | 6/1994 |
| EP | 0 685 749 | 6/1995 |
| EP | 0 771 858 | 9/1996 |
| EP | 0 739 403 | 10/1996 |
| EP | 0 847 432 B | 6/1998 |
| EP | 0 887 398 | 12/1998 |
| EP | 1 213 338 | 6/2002 |
| EP | 1 381 520 B1 | 1/2004 |
| EP | 1 681 586 A1 | 7/2006 |
| EP | 1 894 736 | 8/2007 |
| EP | 1 833 034 A1 | 9/2007 |
| EP | 1876216 | 1/2008 |
| GB | 2 330 139 A | 4/1999 |
| JP | 2003-73600 | 3/2003 |
| RU | 2102246 C1 | 1/1998 |
| RU | 2160928 | 12/2000 |
| RU | 2232422 C2 | 12/2001 |
| RU | 2002130506 A | 7/2004 |
| RU | 2297918 | 3/2005 |
| RU | 2006121650 A1 | 6/2006 |
| RU | 2007109067 A | 3/2007 |
| WO | 96/39307 A1 | 12/1996 |
| WO | 97/39428 | 10/1997 |
| WO | 00/22049 | 4/2000 |
| WO | 01/29137 | 4/2001 |
| WO | 01/95249 | 12/2001 |
| WO | 02/09019 | 1/2002 |
| WO | 02/085642 | 10/2002 |
| WO | 03/084767 | 10/2003 |
| WO | 2004/028824 | 4/2004 |
| WO | 2004/079634 | 9/2004 |
| WO | 2006/063926 | 6/2006 |
| WO | 2007/015261 | 2/2007 |
| WO | 2008/000755 | 1/2008 |
| WO | 2008/110317 A1 | 9/2008 |
| WO | 2008/128714 A1 | 10/2008 |
| WO | 2009/121605 A2 | 10/2009 |

OTHER PUBLICATIONS

International Search Report and Written Opinion for PCT/EP2009/002435 mailed Nov. 16, 2009.
International Preliminary Report on Patentability for PCT/EP2009/002435 mailed Oct. 14, 2010.
U.S. Appl. No. 13/532,277, filed Jun. 25, 2012, Marguerettaz et al.
Chinese Office Action issued with respect to Chinese Application No. 200980120560.8, dated Mar. 5, 2012, with English Translation.
Singaporean Search Report issued with respect to Singaporean Application No. 201007228-8, dated Feb. 21, 2012.
New Zealand Office Action issued with respect to New Zealand Application No. 588366, dated Oct. 12, 2012.
Eurasian Official Action (including English translation) in regards to Eurasian Application No. 201071132, dated Feb. 20, 2014.

* cited by examiner

IDENTIFICATION AND AUTHENTICATION USING POLYMERIC LIQUID CRYSTAL MATERIAL MARKINGS

RELATED APPLICATIONS

The present application is a continuation of U.S. application Ser. No. 13/262,348, which is a National Stage of International Patent Application No. PCT/EP2010/054515, filed Apr. 6, 2010, which is a continuation of U.S. application Ser. No. 12/384,340, filed Apr. 2, 2009, and is a continuation of International Patent Application No. PCT/EP2009/002434, filed Apr. 2, 2009. The disclosures of application Ser. No. 13/262,348, PCT/EP2010/054515, Ser. No. 12/384,340, and PCT/EP2009/002434 are expressly incorporated by reference herein in their entireties.

FIELD OF THE INVENTION

The present invention relates to a machine readable marking for the recognition, identification and authentication of individual items. The marking is made of liquid crystal material, which is applied to a substrate by known variable information printing techniques. The marking is detectable and/or identifiable by passive detecting means, e.g. optical filters under unpolarized (ambient) light, as well as by illumination with polarized light. The marking is applied in the form of indicia, such as a one- or two-dimensional bar code, a matrix code, or the like.

BACKGROUND OF THE INVENTION

"Track and Trace" systems are currently used in different fields of industry. Many industries suffer from counterfeit or diverted products, in particular in the field of mass-produced items such as beverages, perfumes, pharmaceutical drugs, cigarettes, CDs/DVDs, as well as other kind of consumables. Counterfeiting and market diversion are facilitated if the mass products are handled on a lot base, rather than on an individual item base. Counterfeit or diverted products are in such case easily introduced into the supply chain. Producers and retailers would like to be in a position to distinguish their original products from such counterfeit or diverted (parallel imported) products at the level of the individual unit which can be sold.

The underlying technical problem has been addressed in the art through an individual marking of each sellable item introduced into the supply chain. The markings of the prior art were chosen in such a way that they were not susceptible to photocopying, i.e. preferably covert markings were used, which are not visible to the unaided eye or the photocopying machine.

A "Covert" marking, in the context of the present invention, is any marking or security element, which cannot be authenticated by the unaided eye, but which, for authentication, depends on a detecting or reading device of any kind, such as an optical filter or an electronic authentication equipment.

An "Overt" marking, in the context of the present invention, is any marking or security element, which, for authentication, does not depend on a detecting or reading device; i.e. which can be authenticated by the unaided eye.

"Color" in the context of the present invention is used to designate any spectrally selective return of light (electromagnetic radiation) from an illuminated object, be it in the visible, the infrared or in the UV range of the electromagnetic spectrum (i.e. in the whole wavelength range from 200 nm to 2500 nm).

The term "visible" is used to indicate that a property can be revealed by the unaided eye; "detectable" is used for a property that can be revealed by an optical instrument, though not necessarily by the unaided eye, and "invisible" is used for a property that cannot be detected by the unaided eye. In particular, the term "visible color" means a spectrally selective return of light in the wavelength range from 400 nm to 700 nm, which is detectable by the unaided eye.

In the context of the present invention, the terms material and composition are interchangeable.

A first type of individual markings, useful to prevent counterfeit and diversion, is disclosed in U.S. Pat. Nos. 5,569,317, 5,502,304, 5,542,971 and U.S. Pat. No. 5,525,798. According to these documents, a bar code is applied onto the item, using an ink which is not detectable under light of the visible spectrum (400-700 nm wavelength) but which becomes visible when illuminated with light of the UV spectrum (200-380 nm wavelength).

A second type of individual markings is disclosed in U.S. Pat. Nos. 5,611,958 and 5,766,324. According to these documents, a marking is applied onto a commercial good, using an ink which is not detectable in the visible spectrum, but which can be detected through illumination with light of the infrared spectrum (800-1600 nm wavelength).

Yet another type of individual markings, applied through an ink, is disclosed in U.S. Pat. Nos. 5,360,628 and 6,612,494. This marking needs to be illuminated jointly with UV- and IR-light to be revealed.

Still another type of individual marking relies on inks comprising up-converting phosphors such as described in U.S. Pat. No. 5,698,397.

All of the markings mentioned in the cited prior art are covert markings, which are completely invisible to the unaided human eye. The reading of such covert markings depends on a corresponding detecting or reading device, able to detect or read the marking. This can be a disadvantage at the retail center or at the point-of-sale, where an appropriate reading device may not always be available.

Overt markings comprising "optically variable" features, e.g. exhibiting viewing-angle dependent color, have been proposed in the art as authentication means for the "person in the street". Among these are the holograms (cf. Rudolf L. van Renesse, "Optical Document Security" $2^{nd}$ ed., 1998, chapter 10), the optical thin film security devices (idem, chapter 13) and the liquid crystal security devices (idem, chapter 14).

Particularly useful as security devices are the cholesteric liquid crystals. When illuminated with white light, the cholesteric liquid crystal structure reflects light of a determined color, which depends on the material in question and generally varies with the angle of observation and the device temperature. The cholesteric material itself is colorless and the observed color is only due to a physical reflection effect at the cholesteric helical structure adopted at a given temperature by the liquid crystal material. (cf. J. L. Fergason, *Molecular Crystals*, Vol. 1, pp. 293-307 (1966)). In particular liquid crystal materials, the cholesteric liquid crystal polymers (CLCPs), the cholesteric helical structure is "frozen" in a determined state through polymerization, and thus rendered temperature-independent.

If the cholesteric liquid crystal material is applied on a dark or black background, its reflection color is highly apparent to the unaided eye, because the light transmitted by the cholesteric material is largely absorbed by the background, so that the residual backscattering from the background does not disturb the perception of the cholesteric material's own reflection. A careful choice of the background color can thus contribute to the visibility of such an overt marking.

On a clear or white background the reflection color of the cholesteric liquid crystal material is virtually invisible due to the superposition of the cholesteric material's own reflection with the strong backscattering from the background. The cholesteric liquid crystal material can, however, always be identified with the help of a circular polarization filter because it selectively reflects only one of the two possible circular polarized light components, in accordance with its chiral helical structure.

EP-B1-1 381 520 and EP-A1-1 681 586 refer to a birefringent marking and a method of applying the same in the form of a liquid crystal layer having a non-uniform pattern of regions of different thickness. The applied liquid crystal coating or layer may provide for a hidden image on a reflective substrate, which is invisible when viewed under unpolarized light but rendered visible under polarized light or with the help of a polarization filter.

U.S. Pat. No. 5,678,863 refers to means for the identification of documents of value which include a paper or polymer region, said region having a transparent and translucent characteristic. A liquid crystal material is applied to the region to produce an optical effect, which differs when viewed in transmitted and reflected light. The liquid crystal material is in liquid form at room temperature and must be enclosed in a containing means such as microcapsules, in order to be used in a printing process such as gravure, roller, spray or ink-jet printing. The printed liquid crystal region can be in the form of a pattern, for example a bar code. The pattern can be verified by visual or machine inspection of the polarization states of the areas having left-handed and right-handed liquid crystal forms.

U.S. Pat. No. 5,798,147 refers to coating compositions of polymerizable liquid crystal monomers which can be applied by conventional printing processes, such as letterpress, rotogravure, flexographic, offset, screen, and ink-jet printing. The printing inks can be used to produce markings and security inscriptions which are invisible to the human eye. The markings can be detected by their circular polarization or their angle dependent reflection color.

U.S. Pat. No. 6,899,824 refers to a process for printing or coating a substrate with a multilayer of a liquid-crystalline composition and at least one non-liquid-crystalline coating. The process and the printed substrate are useful for producing a counterfeit-proof marking of articles. Preferred methods for applying such printing or coating are screen printing, planographic printing, flexograhic, and letterpress printing.

None of the markings disclosed in the prior art does, however, provide a solution to the technical problem underlying "track & trace" applications, wherein, in addition to a machine-readable individual coding of items with a counterfeit-resistant security marking, an easy authentication of the marking by the unaided eye is required.

"Track & Trace" applications are known in the art for e.g., postal services, wherein each mail piece is individually marked and followed throughout its delivery chain. Barcodes, such as 1D-barcodes, stacked 1D-barcodes, 2D-barcodes or matrix-codes, are most often used as the marking and identification means.

No particular effort is devoted to authentication aspects in the case of the said postal markings, given that the mail piece is handled service-internally by the mailing company throughout the entire delivery chain, so that no authentication is needed. Postal "Track & Trace" applications are merely focused on the identification of the mail piece.

Authentication aspects are, however, of crucial importance in retail applications, where there is a potential risk of substitution of the original goods by counterfeit or diverted ones. For this reason, "Track & Trace" applications in this field must be combined with at least one security element, able to certify the authenticity of the marked good as an original one.

In the following, "Secure Track & Trace" means the combination of a "Track & Trace" application, which allows for the identification of an individual item, with at least one security element, which additionally allows for the authentication of the said item as being genuine.

TECHNICAL PROBLEM

For "Secure Track & Trace" applications, where a good in open circulation must be marked individually as to its authenticity and identity, and followed throughout its life cycle or for a specific period of time, e.g. for liability reasons, there is a need for a marking which is i) uniquely coded, so as to be identifiable ii) machine-readable, iii) copy (counterfeit) resistant, iv) authenticate-able by eye by a human user, and v) authenticate-able by a machine. For particular applications it is furthermore desirable that part of the marking is invisible to the unaided human eye.

SUMMARY OF THE INVENTION

The marking of the present invention, for the secure tracking or tracing of an item or article, comprises a polymeric liquid crystal material having determined optical characteristics, which allow for its authentication and reading by a machine, as well as its authentication by the human eye. The marking is produced on a substrate by a variable information printing process in the form of indicia representing a unique code, which allows for its identification. The marking is further preferably laid out such that part of it is invisible to the unaided human eye.

The marking of the present invention is applied on items or articles such as value documents, banknotes, passports, identity documents, driving licenses, official permissions, access documents, stamps, tax stamps and banderoles, transportation tickets, event tickets, labels, foils, packaging, spare parts, and consumer goods, which thus carry the marking, either directly—applied to their surface—or indirectly—applied to a label applied to their surface.

The polymeric liquid crystal material is preferably of the cholesteric (i.e. twisted nematic) type; for certain applications, nematic (birefringent) liquid crystal material may also be used.

The polymeric liquid crystal material of the marking can either be present as a liquid crystal material polymerized on the surface of a substrate, or alternatively consist of pigment flakes of a liquid crystal polymer, comprised in a coating composition applied on a substrate.

Said substrate can be any type of substrate, woven or non-woven, in particular it can be paper, cardboard, wood, glass, ceramic, metal, plastic, textile, leather, etc.; the substrate may be coated or uncoated, or comprise a sealed or a non-sealed surface.

The polymeric liquid crystal material of the marking preferably comprises further security materials, which are present to increase its resistance towards counterfeiting. These security materials are selected from the group consisting of the inorganic luminescent compounds, the organic luminescent compounds, the IR-absorbers, the magnetic materials, the forensic markers, and combinations thereof.

Said security material can be present as a mere admixture, or, according to the nature of the security material, also as a co-polymerized component of the liquid crystal pigment, of the liquid crystal precursor composition, or of the ink binder. In particular, organic security materials comprising an acrylic or vinylic functionality are easily co-polymerized into a corresponding main polymer. Alternatively, the security material may be grafted, i.e. chemically linked, onto a pre-existing polymer chain.

The substrate, representing the background on which the liquid crystal material is applied, can be of any color; a white background being a preferred option for realizing a marking which is invisible to the unaided eye in the sense that no visible color is observed. A metallic reflecting background is a further preferred option, in particular in the case of a nematic (birefringent) liquid crystal material. The substrate may in general be selected from the group consisting of reflecting substrates, colored substrates, and transparent substrates.

For enabling an easy authentication by a human user, it is preferred that at least part of the background on which the liquid crystal material is applied has a contrasting color, such as red, green, blue or black, which, in combination with the liquid crystal marking, allows to perceive a visible color and an angle-dependent color change by the unaided eye.

Said substrate is thus preferably a patterned substrate, comprising at least two differently colored surface areas, each selected from the group of white surface areas, black surface areas, visibly colored surface areas, reflecting surface areas, transparent surface areas and combinations thereof. It is thus evident to the skilled in the art that the substrate surface carrying the liquid crystal material can have two or more colored areas underneath the liquid crystal material.

The substrate surface, on which the liquid crystal material is applied, can furthermore carry indicia, which may be of any form or color, such as a pattern, an image, a logo, a text, a 1D- or 2D-barcode or a matrix code, etc. The said indicia can be applied by any method of printing or coating.

The substrate can furthermore carry at least one security element selected from the group of inorganic luminescent compounds, organic luminescent compounds, IR-absorbers, magnetic materials, and forensic markers or combinations thereof. The security element can be present in the form of indicia on the substrate surface or be incorporated (embedded) in the substrate itself.

The polymeric liquid crystal material is preferably present in the form of indicia, such as a text or a code. Preferred indicia are chosen from the group comprising 1-dimensional, stacked 1-dimensional, and 2-dimensional barcodes. Current barcode symbologies have been disclosed by Bob Williams in "*Understanding Barcoding*", Pira International Ltd., 2004 (ISBN 1 85802 917 1)

The liquid crystal marking of the present invention is preferably produced by applying a liquid crystal precursor composition to a substrate and hardening the composition in the ordered liquid crystal state. The said precursor composition comprises reactive monomers or oligomers of at least one nematic liquid crystal compound. The reactive monomers or oligomers are preferably UV-cure-able; in this case the applied composition is UV-cured and also comprises a photoinitiator system, as known to the skilled person.

The ordered liquid crystal state depends upon the presence of a chiral dopant. Nematic liquid crystals without chiral dopant arrange in a molecular texture which is characterized by its birefringence. Nematic precursors are known from EP-A-0 216 712, EP-B-0 847 432, and U.S. Pat. No. 6,589,445.

For producing a cholesteric (i.e. twisted nematic) liquid crystal polymer, the said precursor composition must also comprise a chiral dopant. Said dopant may be chosen from the derivatives of isosorbides and isomannides and mixtures thereof according to general formula (I) described below. Isosorbides are known to induce a right helical twist, whereas isomannides are known to induce a left helical twist.

Said dopant induces a helical structure in the nematic liquid crystal compound, characterized by a helical pitch of the order of the wavelength of visible light, leading to light reflection at determined wavelengths, and hence to the appearance of interference color, as well as of angle-dependent color shift. The reflected light from cholesteric liquid crystal phases is circularly polarized (either left-handed or right-handed), according to the rotation sense of the cholesteric helical twist.

The marking of the present invention is obtainable as described in claim 1. In one exemplary embodiment, the liquid crystal precursor composition is first applied to a substrate. The second step involves heating the liquid crystal precursor composition applied onto the substrate to both, evaporate the solvent and promote the desired liquid crystal state. The third step involves hardening the said composition on the substrate in the desired liquid crystal state. However, the skilled artisan will appreciate that the above-mentioned sequence may be modified in any way as will be described further below.

The temperature used to evaporate the solvent and to promote the liquid crystal state depends on the liquid crystal monomer composition. According to the present invention, the temperature is chosen preferably between 55° C. and 150° C. and more preferably between 55° C. and 100° C., most preferably between 60° C. and 100° C. The hardening is preferably performed by subjecting the applied composition to irradiation with UV-light, which induces a polymerization of the reactive monomers or oligomers to form a liquid crystal polymer. The molecular ordering of the liquid crystal is thereby retained, i.e. the nematic or cholesteric texture is fixed in the state which was present during the irradiation. In the case of cholesteric liquid crystal material, the helical pitch, and herewith the optical properties, such as the reflection color and the angle-dependent color shift remain thus fixed.

Another embodiment of the present invention is a marking according to the invention for an item or article, said marking comprising polymeric liquid crystal material having determined optical characteristics wherein said polymeric liquid crystal material produced on the substrate is obtained with a chiral dopant according to general formula (I) disclosed below.

A method for marking an item or article comprises thus the steps of providing a suitable item or article to be marked, and applying at least one polymeric liquid crystal material in the form of indicia representing a unique code by a variable information printing process onto the said item or article. In particular, the unique code represented by the said indicia may be encrypted information, and the method may comprise the step of encrypting the said information.

The said liquid crystal precursor composition can be applied to a substrate by any coating or printing technique. Preferably the composition is applied by a variable information printing process, such as laser printing or ink-jet printing of the continuous or of the drop-on-demand type. Said variable information printing method allows for the unique coding of the marking for each printed item.

For application by ink-jet printing, the composition also comprises an organic solvent, in order to adjust the viscosity value of the composition to be compatible with the chosen printing process, as known to the skilled person.

For application by continuous ink-jet printing, the composition also comprises a conducting agent (salt), which must be soluble in the composition used. Such conducting agent is needed as technical requirement of this printing process, as known to the skilled person.

The composition according to the invention comprises a photoinitiator which must be soluble in the composition used. For example of photoinitiator it can be used α-Hydroxyketone such as 1-Hydroxy-cyclohexyl-phenyl-ketone, a mixture (1:1)1-Hydroxy-cyclohexyl-phenyl-ketone: benzophenone, 2-Hydroxy-2-methyl-1-phenyl-1-propanone or 2-Hydroxy-1-[4-(2-hydroxyethoxy)phenyl]-2-methyl-1-propanone, Phenylglyoxylate such as methylbenzoylformate or a mixture of oxy-phenyl-acetic acid 2-[2 oxo-2 phenyl-acetoxy-ethoxy]-ethyl ester and oxy-phenyl-acetic 2-[2-hydroxy-ethoxy]-ethyl ester, Benzyldimethyl ketal such as Alpha, alpha-dimethoxy-alpha-phenylacetophenone, α-Aminoketone such as 2-Benzyl-2-(dimethylamino)-1-[4-(4-morpholinyl) phenyl]-1-butanone, 2-Methyl-1-[4-(methylthio) phenyl]-2-(4-morpholinyl)-1-propanone, Phosphine oxide derivatives such as Diphenyl (2,4,6-trimethylbenzoyl)-phosphine oxide or Phosphine oxide, phenyl bis(2,4,6-trimethylbenzoyl) supplied by Ciba, and also thioxanthone derivatives such as Speedcure ITX (CAS 142770-42-1), Speedcure DETX (CAS 82799-44-8), Speedcure CPTX (CAS 5495-84-1-2 or CAS 83846-86-0) supplied by Lambson.

The composition according to the invention could also comprise a silane derivative which must be soluble in the composition used. For example of silane derivatives it can be used vinylsilane derivatives such as vinyltriethoxysilane, vinyltrimethoxysilane, vinyltris(2-methoxyethoxy)silane, 3-Methacryloxypropyltrimetho xysilane, Octyltriethoxysilane or 3-Glycidyloxypropyl triethoxysilane from Dynasylan® family supplied by Evonik.

In general, the method for authenticating an item or article carrying a marking according to the present invention comprises the steps of a) providing an item or article carrying a marking according to the present invention, b) illuminating the marking on said item or article with at least one quality of light from at least one light source, c) detecting the said marking's optical characteristics through the sensing of light reflected by the marking, d) determining the item's or article's authenticity from the detected optical characteristics of the marking.

The marking of the present invention can be authenticated according to a first method by simple visual inspection under ambient light. To this aim, the background, on which the liquid crystal material is applied, must provide sufficient optical contrast, so as to allow the human observer to perceive the reflected color and the color shift of the liquid crystal material. Depending on the background, part of the marking may remain virtually invisible to the unaided eye.

In a second method, the marking is authenticated under ambient light with the help of a passive detecting means such as an optical filter. A preferred such passive detecting means is a left-handed or a right-handed circular polarizing filter, or a juxtaposition of both. This allows determining the rotation sense of the helical pitch of the cholesteric liquid crystal material by determining the polarization state of the light reflected by the said material. Optionally, the polarization filter can be combined with color filters, in order to reduce the spectral bandwidth to the spectral reflection band of the liquid crystal material, and hence to reduce background contributions. More than one optical filter may be used in conjunction.

In a third method, the marking is authenticated with the help of circular polarized light from at least one polarized light source. The liquid crystal material reflects differently light of different circular polarization; hence materials of left and of right helical pitch can be distinguished by their respective response to circularly polarized light. The illumination of the marking by the polarized light source, as well as the observation of the reflected light from the marking, may optionally be performed through a color filter. More than one polarized light sources may be used in conjunction.

In a fourth method, the marking is authenticated with the help of an electro-optical authentication device. In a first embodiment, said device comprises at least one photocell, in combination with a circular polarization filter and/or with a circular polarized light source. In another embodiment said device comprises an electro-optic camera, such as a linear CCD sensor array, a 2-dimensional CCD image sensor array, a linear CMOS image sensor array, or a 2-dimensional CMOS image sensor array, in combination with a circular polarization filter and/or with a circular polarized light source.

Optionally, the circular polarization filter or the circular polarized light source in the above embodiments can be combined with color filters, to select a particular spectral domain and to enhance the contrast ratio of the light reflected from the liquid crystal material to the light reflected from the background.

The circular polarization filters can generally also be replaced by an electro-optic polarization switch. Such device is known in the art, e.g. from DE 102 11 310 B4, and allows to select one or the other circular polarization state by an applied corresponding voltage.

In all cases of cholesteric liquid crystal materials, the marking of the present invention is authenticated by verifying one or more of its characteristic properties, namely the circular polarization state and/or the viewing-angle dependent color of the reflected light from the marking. The polarized light source or the polarized light detection equipment or both may be chosen to operate in the visible, the infrared, or the UV region of the electromagnetic spectrum, or in a combination of these, according to the optical characteristics of the marking.

The marking of the present invention can be identified by reading the indicia it represents and by subsequently correlating the information so retrieved from the marking with information stored in a data base. In a particular embodiment, the information represented by the indicia of the marking is encrypted, and said identification comprises the step of decrypting said information. Preferably, the indicia are read by an electro-optic camera, such as a CCD- or a CMOS-image sensor array.

In general, the method for identifying an item or article carrying a marking according to the present invention comprises the steps of a) providing an item or article carrying a marking according to the present invention, b) illuminating the marking on said item or article with at least one quality of light from at least one light source, c) reading the indicia represented by the marking, deriving corresponding information, d) correlating the information retrieved from the indicia of the marking with information stored in a data base, e) obtaining confirmation or denial concerning the item's or articles identity.

The identification of an item or article carrying a marking according to the present invention can be performed with the same reading equipment configuration or assembly which is used for the authentication.

In a first embodiment the said indicia are represented by a 1-dimensional or a 2-dimensional barcode, and the image retrieved by the electro-optic camera in digital form is analyzed using a corresponding algorithm. The information contained in the barcode is retrieved, if necessary, decrypted, and compared with information stored in a data base, hereby identifying the item, and optionally updating the data base with supplementary information, e.g. about the item's history. The camera may be part of a reading device equipped with own communication capabilities, or part of a communication device, such as a mobile phone, the retrieval of the information taking place using the mobile phone's internal resources. The data base may be either located in the communication device (built-in or exchangeable memory), or on an external server reached via a communication network.

In a second embodiment the said indicia are represented by an alphanumeric code, and the image retrieved by the electro-optic amera (reading device) in digital form is analyzed using a corresponding optical character recognition (OCR) algorithm. The information contained in the code is retrieved and compared with information stored in a data base, hereby identifying the item, and optionally updating the data base. As in the first embodiment, the data base may be either located in the reading device (built-in or exchangeable memory), or on an external server reached via a communication network. The alphanumeric code can be printed using a standard font or a special machine identifiable font. Alternatively, the alphanumeric code can be visually read and either sent via a communication system (e.g. Internet or SMS) to a data center for validation or checked against data provided with the item in form of a label, reference mark or another alphanumeric code.

The marking of the present invention, made of polymeric liquid crystal material having determined optical characteristics, can be used for the secure tracking and tracing of items, articles or goods with an individualized, counterfeit-resistant code for the secure tracking and tracing of said items, articles or goods.

The application of an individualized code onto a good or item requires a variable information printing process. A preferred variable information printing process in the context of the present invention is chosen from the group of continuous ink-jet printing and drop-on-demand ink-jet printing; these printing processes allow for a rapid, non-contact application of said individualized code onto any kind of surfaces. Said individualized code allows the identification of each single item at a later stage of its life cycle.

In order to prevent the substitution of the original item by a counterfeit carrying a copy of said individualized code, said individualized code must be counterfeit-resistant. Counterfeit resistance can be provided through a particular security material having particular physical, preferably optical, properties; the said material can be either constitutive or incorporated in the marking. The particular security material can be a polymeric liquid crystal material having determined optical characteristics, or an additive selected from the group of the inorganic luminescent compounds, the organic luminescent compounds, the IR-absorbers, the magnetic materials, the forensic markers, and combinations thereof.

The marking of the present invention can be used on items or articles, such as value documents, banknotes, passports, identity documents, driving licenses, official permissions, access documents, stamps, tax stamps and banderoles (in particular for tobacco products and alcoholic beverages), transportation tickets, event tickets, labels, foils, packaging (in particular for pharmaceutical products), and in general for marking spare parts and consumer goods (in particular to address liability issues).

The marking of the present invention, applied to items, goods, or articles is suitable for use in the secure tracking and tracing of such marked items, goods or articles. Such secure tracking and tracing of an item or article comprises noteworthy the first commutable steps of a) applying a marking according to the invention to the item or article to be traced; and b) storing information related to the marked item or article in a data base; as well as the second commutable steps of c) authenticating the item or article according to the authentication method disclosed herein; and d) identifying the item or article, according to the identification method disclosed herein, using the information previously stored in the data base. Optionally the data base may hereby be updated with new information elements related to the item or article.

The code applied to the item or good represents digital information, which is stored in a data base, in order to identify the item or good at a later stage. Said code may be encrypted, so as to protect the information it contains upon transmission from and to the data base. Said data base can be part of a data base management system. All kind of encryption algorithms are suitable, e.g. a public-private key of the RSA type.

Said data base may be a local data base, integrated into the authentication device. Alternatively, it may be a remote data base, linked to the authentication device through a wired or wireless connection. A local data base may also be updated regularly from a remote server.

In a further aspect, the present invention provides for the application of the individual marking by a variable-information printing process. Preferred is ink-jet printing, either using the continuous ink-jet, or the drop-on-demand (DOD) ink-jet or valve-jet printing process. Industrial ink-jet printers, commonly used for numbering and coding applications on conditioning lines and printing presses, are particularly suitable. Preferred ink-jet printers are single nozzle continuous ink-jet printers (also called raster or multi level deflected printers) and drop-on-demand ink-jet, in particular valve-jet, printers.

To provide for an entirely covert and machine readable marking, nematic liquid crystal materials are used. To provide for an overt or semi-covert and machine readable marking, cholesteric or chiral-nematic liquid crystal materials are used.

DESCRIPTION OF THE DRAWINGS

For a more complete understanding of the present invention reference is made to the detailed description of the invention and the attached drawings.

Figure 1:
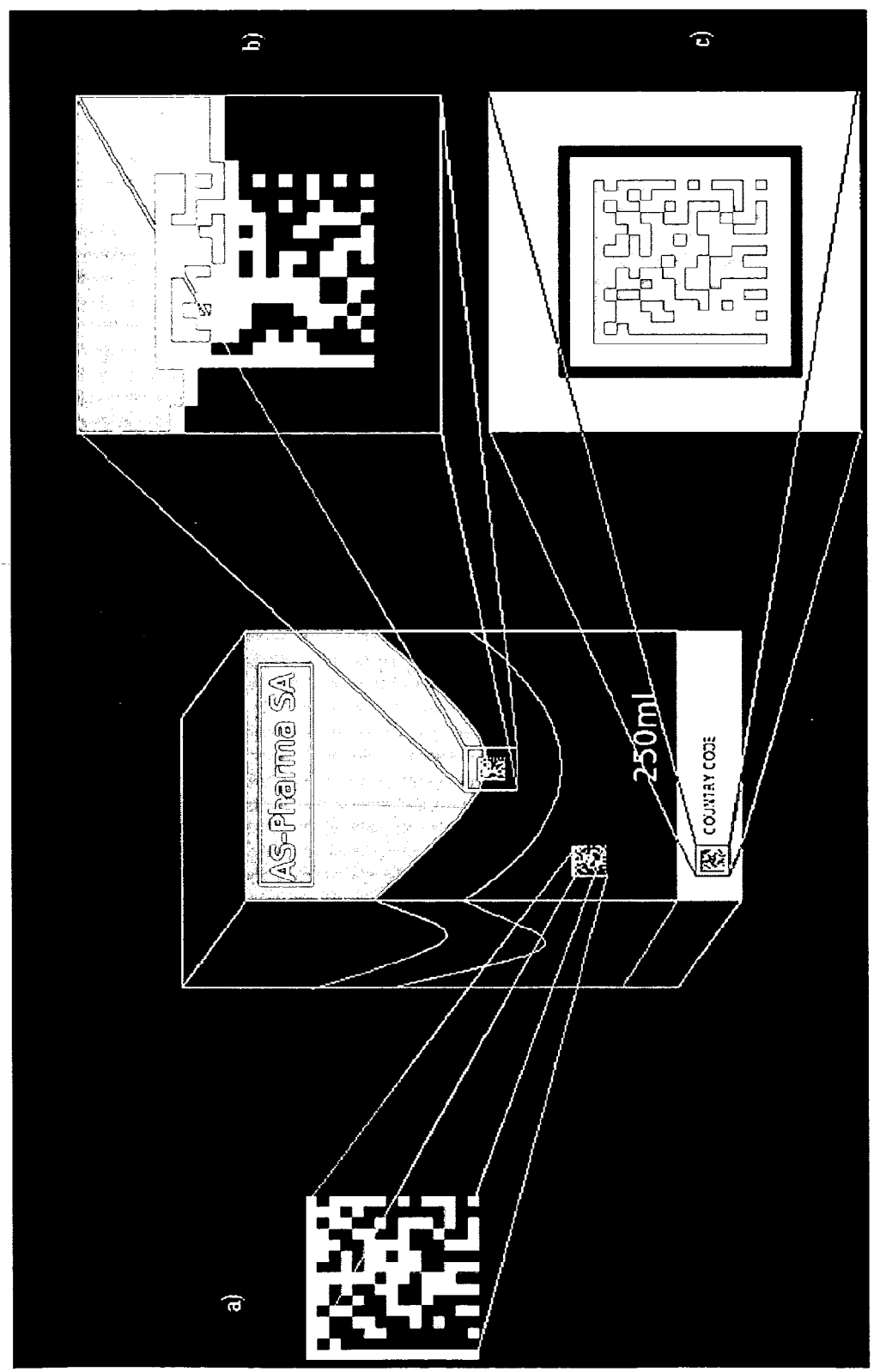
FIG. 1 schematically depicts a cardboard packaging, e.g. a pharmaceutical packaging, carrying representative markings a), b), c) according to the invention, which are printed with liquid crystal material at different locations on said cardboard packaging:
  a) shows a Data Matrix code on a particularly dark colored background, e.g. a black background;
  b) shows a Data Matrix code on a background of mixed color, e.g. having dark and light colored parts;
  c) shows a Data Matrix code on a white background.
Figure 2A:
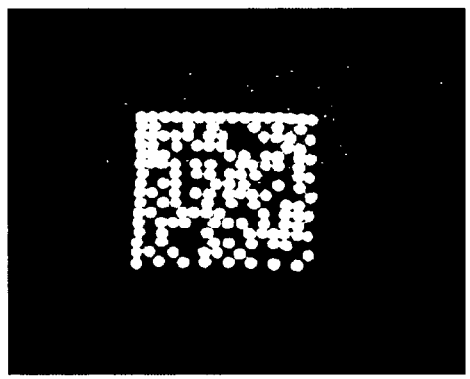
FIG. 2 shows images captured from an ECC200 data matrix code printed with UV-cured liquid crystal (LC) material on coated cardboard:
  a) LC Data Matrix code retrieved from a black background, under right-circular polarized white light illumination, having a right-circular polarizing filter in front of the CMOS camera.
  b) LC Data Matrix code retrieved from a black/white background, under right-circular polarized white light illumination, having a right-circular polarizing filter in front of the CMOS camera.
Figure 2B:
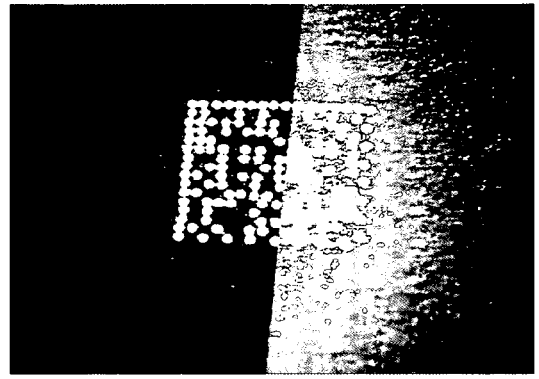
Figure 2C:
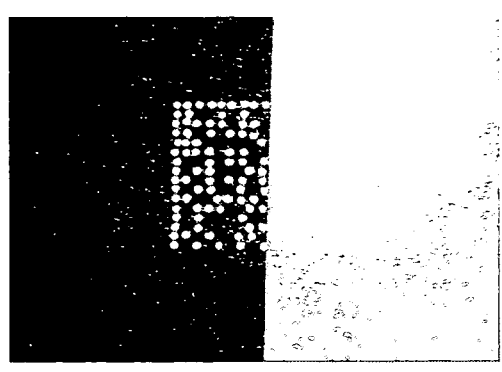
Figure 2D:
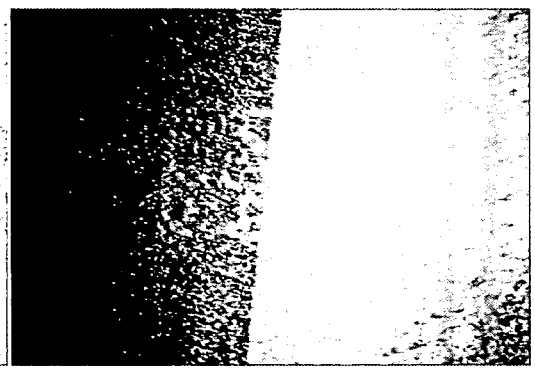

c) LC Data Matrix code retrieved from a black/white background, under right-circular polarized white light illumination, having no filter in front of the CMOS camera.

d) LC Data Matrix code retrieved from a black/white background, under unpolarized white light illumination, having no filter in front of the CMOS camera.

DETAILED DESCRIPTION OF THE INVENTION

In a first embodiment, the marking of the present invention is made of a liquid crystal precursor composition, which is obtainable by independently applying a liquid crystal precursor composition to a substrate by a variable information printing process, applying heat to both evaporate the solvent contained in the liquid crystal precursor composition and promote the liquid crystal state, and hardening the applied composition in the ordered liquid crystal state. In one exemplary embodiment, the liquid crystal precursor composition is applied to the surface of a substrate. Heat is then applied to both, evaporate the solvent and promote the liquid crystal state. The composition in the liquid crystal state is then polymerized (cured) by irradiation with UV light or with electron beam radiation, as known by the skilled in the art. In an alternative exemplary embodiment, the heat is applied to the whole body of substrate and liquid crystal precursor composition or only to the substrate, if it is able to transmit the applied heat to the liquid crystal precursor composition. In a further alternative embodiment, the liquid crystal precursor composition may be subjected to heat before applying it to the substrate. In an additional alternative embodiment, the step of heating the liquid crystal precursor composition and applying it to a substrate may be performed in a single step.

The liquid crystal material applied in this embodiment is thus a monomeric or oligomeric precursor of a liquid crystal polymer. Said precursor comprises at least one nematic liquid crystal monomer or oligomer, said monomer or oligomer having polymerizable groups. Suitable nematic liquid crystal monomers or oligomers are from the group of bisacrylates such as 2-methyl-1,4-phenylene bis(4-(4-(acryloyloxy)butoxy)benzoate);

1,4-phenylene bis(4-(4-(acryloyloxy)butoxy)benzoate);

2-methyl-1,4-phenylene bis(4-(6-(acryloyloxy)hexyloxy)benzoate);

1,4-phenylene bis(4-((4-(acryloyloxy)butoxy)carbonyloxy)benzoate);

2-methyl-1,4-phenylene bis(4-((4-(acryloyloxy)butoxy) carbonyloxy)benzoate);

and the combinations thereof.

The nematic liquid crystal monomer or oligomer may be present in the precursor material in a range of 10% to 100% by weight.

Suitable stabilizers are Florstab UV-1 supplied by Kromachem, and Genorad 16 supplied by Rahn.

The photoinitiator may be present in the precursor material in a range of 0.5% to 5% by weight.

For obtaining cholesteric (i.e. twisted nematic) phases, said precursor further comprises at least one chiral dopant (chiral inducer). Suitable chiral dopants comprise the derivatives of isomannide and of isosorbide, represented by the general formula (I)

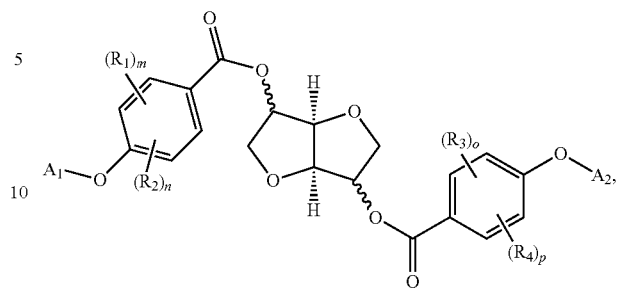
(I)

wherein $R_1$, $R_2$, $R_3$, $R_4$, $R_5$, $R_6$, $R_7$ and $R_8$ denote each independently $C_1$-$C_6$ alkyl, $C_1$-$C_6$ alkoxy;

$A_1$ and $A_2$ denote each independently a group:
i) —[(CH$_2$)y-O]z-C(O)—CH═CH$_2$;
ii) —C(O)-D$_1$-O—[(CH$_2$)y-O]z-C(O)—CH═CH$_2$;
iii) —C(O)-D$_2$-O—[(CH$_2$)y-O]z-C(O)—CH═CH$_2$;

D$_1$ denotes a group

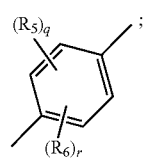

D$_2$ denotes a group

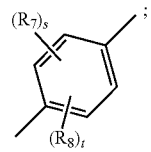

m, n, o, p, q, r, s, and t denote each independently 0, 1, 2;
y denotes 0, 1, 2, 3, 4, 5, 6;
z equal 0 if y equal 0 and z equal 1 if y equal 1 to 6.

In another embodiment chiral dopants comprise the derivatives of isomannide represented by the formula (IA)

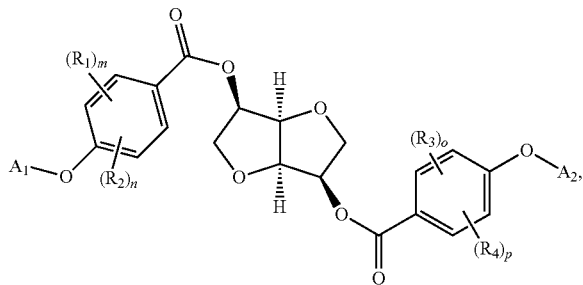
(IA)

wherein $R_1$, $R_2$, $R_3$, $R_4$, $R_5$, $R_6$, $R_7$ and $R_8$ denote each independently $C_1$-$C_6$ alkyl, $C_1$-$C_6$ alkoxy;

A₁ and A₂ denote each independently a group:
i) —[(CH₂)y-O]z-C(O)—CH═CH₂;
ii) —C(O)-D₁-O—[(CH₂)y-O]z-C(O)—CH═CH₂;
iii) —C(O)-D₂-O—[(CH₂)y-O]z-C(O)—CH═CH₂;
D₁ denotes a group

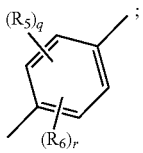

D₂ denotes a group

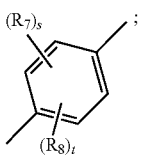

m, n, o, p, q, r, s, and t denote each independently 0, 1, 2;
y denotes 0, 1, 2, 3, 4, 5, 6;
z equal 0 if y equal 0 and z equal 1 if y equal 1 to 6.

In a preferred embodiment, in formula (IA), R₁, R₂, R₃, R₄, R₅, R₆, R₇ and R₈ denote each independently C₁-C₆ alkyl. In an alternative embodiment, in formula (IA), R₁, R₂, R₃, R₄, R₅, R₆, R₇ and R₈ denote each independently C₁-C₆ alkoxy.

In a further preferred embodiment, in formula (IA), A₁ and A₂ denote each independently i) —[(CH₂)y-O]z-C(O)—CH═CH₂; R₁, R₂, R₃ and R₄ denote each independently C₁-C₆ alkyl; and m, n, o, and p denote each independently 0, 1, 2. In an alternative embodiment, in formula (IA), A₁ and A₂ denote each independently i) —[(CH₂)y-O]z-C(O)—CH═CH₂; R₁, R₂, R₃ and R₄ denote each independently C₁-C₆ alkoxy; and m, n, o, and p denote each independently 0, 1, 2.

In other preferred embodiment of formula (IA), A₁ and A₂ denote each independently ii) —C(O)-D₁-O—[(CH₂)y-O]z-C(O)—CH═CH₂ and/or iii) —C(O)-D₂-O—[(CH₂)y-O]z-C(O)—CH═CH₂; and R₁, R₂, R₃, R₄, R₅, R₆, R₇ and R₈ denote each independently C₁-C₆ alkyl. In an alternative embodiment, in formula (IA), A₁ and A₂ denote each independently ii) —C(O)-D₁-O—[(CH₂)y-O]z-C(O)—CH═CH₂ and/or iii) —C(O)-D₂-O—[(CH₂)y-O]z-C(O)—CH═CH₂; and R₁, R₂, R₃, R₄, R₅, R₆, R₇ and R₈ denote each independently C₁-C₆ alkoxy.

In another embodiment chiral dopants comprise the derivatives of isosorbide represented by the formula (IB)

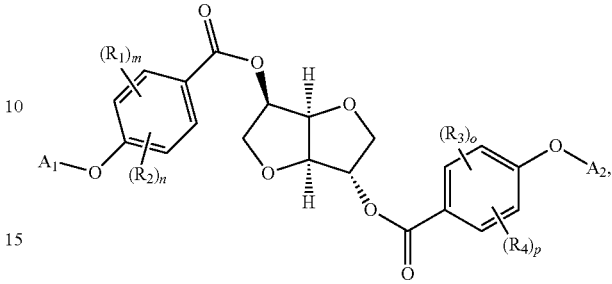

wherein
R₁, R₂, R₃, R₄, R₅, R₆, R₇ and R₈ denote each independently C₁-C₆ alkyl, C₁-C₆ alkoxy;
A₁ and A₂ denote each independently a group:
i) —[(CH₂)y-O]z-C(O)—CH═CH₂;
ii) —C(O)-D₁-O—[(CH₂)y-O]z-C(O)—CH═CH₂;
iii) —C(O)-D₂-O—[(CH₂)y-O]z-C(O)—CH═CH₂;
D₁ denotes a group

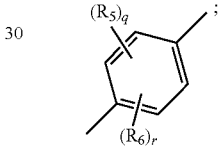

D₂ denotes a group

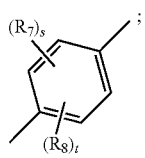

m, n, o, p, q, r, s, and t denote each independently 0, 1, 2;
y denotes 0, 1, 2, 3, 4, 5, 6;
z equal 0 if y equal 0 and z equal 1 if y equal 1 to 6.

In a preferred embodiment, in formula (IB), R₁, R₂, R₃, R₄, R₅, R₆, R₇ and R₈ denote each independently C₁-C₆ alkyl. In an alternative embodiment, in formula (IB), R₁, R₂, R₃, R₄, R₅, R₆, R₇ and R₈ denote each independently C₁-C₆ alkoxy.

In a further preferred embodiment, in formula (IB), A₁ and A₂ denote each independently i) —[(CH₂)y-O]z-C(O)—CH═CH₂; R₁, R₂, R₃ and R₄ denote each independently C₁-C₆ alkyl; and m, n, o, and p denote each independently 0, 1, 2. In an alternative embodiment, in formula (IB), A₁ and A₂ denote each independently i) —[(CH₂)y-O]z-C(O)—CH═CH₂; R₁, R₂, R₃ and R₄ denote each independently C₁-C₆ alkoxy; and m, n, o, and p denote each independently 0, 1, 2.

In other preferred embodiment, in formula (IB), A₁ and A₂ denote each independently ii) —C(O)-D₁-O—[(CH₂)y-O]z-C(O)—CH═CH₂ and/or iii) —C(O)-D₂-O—[(CH₂)y-O]z-C(O)—CH═CH₂; and R₁, R₂, R₃, R₄, R₅, R₆, R₇ and R₈ denote each independently C₁-C₆ alkyl. In an alternative embodiment, in formula (IB), $A_1$ and $A_2$ denote each independently ii) —C(O)-$D_1$-O—[($CH_2$)y-O]z-C(O)—CH=$CH_2$ and/or iii) —C(O)-$D_2$-O—[($CH_2$)y-O]z-C(O)—CH=$CH_2$; and $R_1$, $R_2$, $R_3$, $R_4$, $R_5$, $R_6$, $R_7$ and $R_8$ denote each independently $C_1$-C6 alkoxy.

In a preferred embodiment, in the formulae (I), (IA) and/or (IB), the alkyl or alkoxy group of $R_1$, $R_2$, $R_3$, $R_4$, $R_5$, $R_6$, $R_7$ and $R_8$ may comprise 4 or 6 carbon atoms.

Alkyl groups comprising 4 carbon atoms may be selected from the group comprising butyl or isopropyl. Alkyl groups comprising 6 carbon atoms may be selected from the group comprising hexyl, 2-methylpentyl, 3-methylpentyl, 2,2-dimethylpentyl or 2,3-dimethylpentyl.

Alkoxy groups comprising 4 carbon atoms may be selected from the group comprising but-1-oxy, but-2-oxy, isopropoxy or tert-butoxy. Alkoxy groups comprising 6 carbon atoms may be selected from the group comprising hex-1-oxy, hex-2-oxy, hexan-3-ol, 2-methylpentan-1-ol, 2-methylpentan-2-ol, 2-methylhydroxypentane, 2-methylpent-3-oxy, 2-methylpent-4-oxy, 4-methylpent-1-oxy, 3-methylpent-1-oxy, 3-methylpent-2-oxy, 3-methylpent-3-oxy, 3-methylhydroxypentane, 2,2-dimethylpent-1-oxy, 2,2-dimethylpent-3-oxy, 2,2-dimethylpent-4-oxy, 4,4-dimethylpent-1-oxy, 2-methyl-2-methylhydroxypentane, 2,3-dimethylpent-1-oxy, 2,3-dimethylpent-2-oxy, 2,3-dimethylpent-3-oxy, 2,3-dimethylpent-4-oxy, 3,4-dimethylpentl-oxy, 2-methylhydroxy-3-methylpentane or 2-methyl-3-methylhydroxypentane.

Chiral dopant according to the invention include in particular those selected from the following group:
(3R,3aR,6R,6aR)-hexahydrofuro[3,2-b]furan-3,6-diyl bis(4-(4-(acryloyloxy)benzoyloxy)benzoate);
(3R,3aR,6R,6aR)-hexahydrofuro[3,2-b]furan-3,6-diyl bis(4-(4-(acryloyloxy)butoxy)benzoate);
(3R,3aR,6R,6aR)-hexahydrofuro[3,2-b]furan-3,6-diyl bis(4-(acryloyloxy)-2-methylbenzoate);
(3R,3aR,6S,6aR)-hexahydrofuro[3,2-b]furan-3,6-diyl bis(4-(4-(acryloyloxy)benzoyloxy)-3-methoxybenzoate);
(3R,3aR,6R,6aR)-hexahydrofuro[3,2-b]furan-3,6-diyl bis(4-(4-(acryloyloxy)-3-methoxybenzoyloxy)benzoate);
(3R,3aR,6R,6aR)-6-(4-(4-(acryloyloxy)-3-methoxybenzoyloxy)-3-methoxybenzoyloxy)hexahydro furo[3,2-b]furan-3-yl 4-(4-(acryloyloxy)benzoyloxy)-3-methoxybenzoate;
(3R,3aR,6R,6aR)-hexahydrofuro[3,2-b]furan-3,6-diyl bis(4-(4-(acryloyloxy)-3-methoxybenzoyloxy)-3-methoxybenzoate); and
(3R,3aR,6R,6aR)-hexahydrofuro[3,2-b]furan-3,6-diyl bis(4-(acryloyloxy)benzoyloxy)-3-methoxybenzoate).

The chiral dopant may be present in the precursor material in a range of 0.1% to 25% by weight.

A variable information printing process is used to apply the liquid crystal precursor material to the substrate. The term "variable information printing" encompasses also variable data printing. This form of printing process is a printing process in which elements such as text, graphics or images may be changed from one printed piece to the next, allowing the "mass-customization" of items as opposed to the "mass-production" of a single item, e.g. using offset lithography, without delaying or stopping the press being necessary. A basic design is developed which comprises various sections which may be altered using a database of information that fills in the changeable fields according to the demand and intention of the user. Depending on the number of changeable fields, the final product is more or less sophisticated, e.g. like a marking according to the present invention. The elements and/or sections to be changed on each individual item can be determined in advance and controlled in each moment.

The marking is preferably applied by ink-jet printing, either of the continuous ink-jet or of the drop-on-demand ink-jet type, preferably by single nozzle/raster. For application by ink-jet printing, the composition must further contain a solvent, in order to adjust its viscosity to the low values required by the said printing processes. Typical viscosity values for ink-jet printing inks are in the range of 4 to 30 mPa·s at 25° C. Solvents, which can be used are chosen from the group of the low-viscosity, slightly polar and aprotic organic solvents, such as methyl-ethyl-ketone (MEK), acetone, ethylacetate, ethyl 3-ethoxypropionate or toluene. Chlorinated solvents like dichloromethane, trichloromethane or trichloroethylene are technically suitable, but not desirable in printing inks because of their toxicity.

The solvent is comprised in the ink-jet precursor material in a range of 10% to 95%, typically 45% to 85% by weight.

In the case of continuous ink-jet printing, the precursor material also comprises a dissolved conducting agent, typically a salt, such as lithium nitrate, lithium perchlorate, tetrabutylammonium chloride or tetrabutylammonium tetrafluoroborate.

The salt is present in a concentration range of 0.1 to 5% by weight.

The precursor material preferably may further comprise security materials, which are present in low to moderate concentration, in order to increase the resistance of the marking towards counterfeiting. These security materials are selected from the group consisting of the inorganic luminescent compounds, the organic luminescent compounds, the IR-absorbers, the magnetic materials, the forensic markers, and combinations thereof. Concentration ranges are 0.01% to 5% for luminescent compounds, 0.1% to 10% for IR-absorbers or magnetic materials, and 0.001% to 1% for forensic marker materials.

The preferred cholesteric liquid crystal precursor material for carrying out the present invention using ink-jet printing equipment comprises a mixture of at least one nematic compound, at least one chiral inducer compound according to formula (I), (IA) or (IB), an organic solvent, and a photoinitiator.

Said nematic compound is preferably of the acrylic- or bis-acrylic type as disclosed in EP-A-0 216 712 and EP-B-0 847 432, U.S. Pat. No. 6,589,445, which are herein included by reference. The preferred amount of the nematic compound present in the cholesteric liquid crystal precursor mixture is from about 10 wt % to about 60 wt %, more preferably from about 10 wt % to about 45 wt %.

The amount of the chiral inducer present in the cholesteric liquid crystal precursor mixture ranges from about 0.1 wt % to about 25 wt %, preferably from about 0.5 wt % to about 15 wt %.

The liquid crystal precursor material for producing a marking according to the present invention may further comprise dyes, pigments, coloring agents, diluents, conducting salts, surface-active compounds, surface adhesion promoters, wetting agents, defoamers, and dispersing agents.

The marking of the present invention is preferably applied in the form of indicia representing a unique 1-dimensional, a stacked 1-dimensional, or a 2-dimensional barcode or matrix code. The symbology is preferably chosen among those used in the retail industry for the marking of commercial goods. These symbologies are internationally recognized standards, and the corresponding reading and decoding algorithms are known and implemented in commercially available devices.

Suitable 1-dimensional and stacked 1-dimensional barcode symbologies are known to the skilled person and available under symbology names such as Plessey, U.P.C., Codabar, Code 25—Non-interleaved 2 of 5, Code 25—Interleaved 2 of 5, Code 39, Code 93, Code 128, Code 128A, Code 128B, Code 128C, Code 11, CPC Binary, DUN 14, EAN 2, EAN 5, EAN 8, EAN 13, GS1-128 (formerly known as UCC/EAN-128), EAN 128, UCC 128, GS1 DataBar formerly Reduced Space Symbology (RSS), ITF-14, Pharmacode, PLANET, POSTNET, OneCode, MSI, PostBar, RM4SCC/KIX, or Telepen.

Suitable 2-dimensional barcode symbologies are known to the skilled person and available under symbology names such as 3-DI, ArrayTag, Aztec Code, Small Aztec Code, bCODE, Bullseye, Codablock, Code 1, Code, 16K, Code 49, Color code, CP Code, DataGlyphs, Datamatrix, Datastrip Code, Dot Code A, EZcode, High Capacity Color Barcode, Hue-Code, INTACTA.CODE, InterCode, MaxiCode, mCode, MiniCode, PDF417, Micro PDF417, PDMark, PaperDisk, Optar, QR Code, Semacode, SmartCode, Snowflake Code, ShotCode, SuperCode, Trillcode, UltraCode, VeriCode, VSCode, WaterCode, and ECC200. This latter has a built-in error correction code and is defined in international standard ISO/CEI 16022:2006.

Suitable font types for optical character recognition (OCR) are known to the skilled person.

FIG. 1 schematically shows a product packaging having a cholesteric liquid crystal marking of the present invention. The marking is present in the form of a ECC200 data matrix code on the surface of said packaging. Data Matrix ECC200 is a public domain symbology. The marking can be applied to any desired position on the packaging. Thus it can be present wholly on a first background color (a), or partially, overlapping with a first background color and a second design color motive present on the packaging (h), or wholly be present on a white or colorless region of the packaging (c).

The reading device for reading the marking of the present invention can be constructed on the basis of commercially available barcode readers, in particular on the basis of hand-held CCD/CMOS-camera reading equipment and reading stations used in the retail industry. In case of an appropriate matching of the marking with the available (narrow-band) illumination, said reading equipment may be directly enabled to read the liquid crystal codes.

In other cases, the reading device can be further adapted (enabled) so as to read the response of the specific security elements implemented in the marking. Correspondingly adapted flat-bed scanners can also be used. CCD-camera based barcode readers are known to the skilled person and are produced by several industrial companies, such as AccuSort, Cognex, DVT, Microscan, Omron, Sick, RVSI, Keyence, etc.

Said adaptation of the reading device may comprise the implementation of one or several optical filters chosen from the group of linear polarizing filters, right-circular polarizing filters, left-circular polarizing filters, electro-optic polarization filters, wave-plates, and spectrally selective color filters of any type, and combinations thereof.

In a particular embodiment at least two different optical filters are used. Said adaptation may further comprise the implementation of one or several particular light sources chosen from the group of spectrally selective (i.e. colored) light sources, linear polarized light sources, left- and right-circular polarized light sources, and combinations thereof.

The light sources, however, can be chosen from ambient light, incandescent light, laser diodes, light emitting diodes, and all type of light sources having color filters. Said light sources may have an emission spectrum in the spectral domain of the visible light (400-700 nm wavelength), the near optical infrared (700-1100 nm wavelength), the far optical infrared (1100-2500 nm wavelength), or the UV (200-400 nm wavelength) region of the electromagnetic spectrum.

Said reading device is thus not only enabled to read the marking, but also to authenticate it as being made of the correct security material, i.e. comprising the required security elements. Said reading device delivers a digital information representative of the code which has been read, and pointing towards an entry in a data base corresponding to the item carrying the said marking and code.

Said digital information may be compared with information stored in the reading device or may be exchanged between the reading device and an external data base; the exchange can take place in encrypted form, using e.g. a public/private encoding of the RSA type. Said exchange of information can take place by all kind of transmission means, e.g. wire-bound transmission, wireless radio link, infrared-link, etc.

Said coating composition may preferably comprise further security materials, which are present in low to moderate concentration, in order to increase its resistance towards counterfeiting. These security materials are selected from the group consisting of the inorganic luminescent compounds, the organic luminescent compounds, the IR-absorbers, the magnetic materials, the forensic markers, and combinations thereof. Typical concentration ranges are 0.01% to 5% for luminescent compounds, 0.1% to 10% for IR-absorbers or magnetic materials, and 0.001% to 1% for forensic marker materials.

To accommodate particular conditions, the coating composition for producing a marking according to the present invention may further comprise dyes, pigments, coloring agents, diluents, conducting salts, surface-active compounds, surface adhesion promoters, wetting agents, defoamers, and dispersing agents, as known in the art.

The authentication and identification of the liquid crystal marking according to the present invention requires a light source and must be done in one of the following ways:
 i) by illuminating the marking with circular or linear polarized light and detecting the marking's reflection;
 ii) by illuminating the marking with unpolarized (e.g. ambient) light and detecting the marking's reflection through a circular or linear polarizing filter,
 iii) by a combination of circular or linear polarized illumination and detection through a circular or linear polarizing filter.

The illumination of a marked item or article is thus performed by a light source chosen from unpolarized light sources, linear polarized light sources, left circular polarized light sources, and right circular polarized light sources.

In all cases, detection may be performed by eye or with the help of electro-optic detection equipment, such as a photocell, or a CCD or CMOS camera. The light sources and the detection may be made or chosen spectrally selective through the use of particular light emitters and/or color filters. The detection is preferably carried out in the visible region (400-700 nm wavelength) of the electromagnetic spectrum.

In a particular embodiment the illumination of the marking for authenticating an item or article, is performed using at least two different light sources selected from non-polarized (randomly polarized) light sources, linear polarized light sources, left circular polarized light sources, and right circular polarized light sources.

FIG. 2 shows images taken from ECC200 Data matrix codes printed with liquid crystal material on coated cardboard. These images clearly illustrate the advantage of using the polarizing properties of the liquid crystal material marking for the reading of the printed code on a clear or structured background. Most advantageous is a combination of polarized light for illumination and the use of a polarizing filter in front of the camera. All images were taken with the same light source and with the same camera settings, all in black and white mode, and with or without polarizing filters before the light source and/or the camera. The images were digitally treated for maximum contrast and optimum brightness.

In a preferred option, the liquid crystal marking of the present invention is rendered visible under unpolarized (preferably ambient) light by a passive detecting means such as a linear or a circular polarizing filter. The marking can, however, also be identified and authenticated outside the visible spectrum (400-700 nm wavelength), e.g. in the infrared region (700 to 2500 nm wavelength), preferably in the near optical infrared (700-1100 nm wavelength), in the far optical infrared (1100-2500 nm wavelength) or in the UV (200-400 nm wavelength) region of the electromagnetic spectrum, given that the marking has a reflection band in these regions.

The cholesteric liquid crystal polymer is, by its nature, a spectrally selective reflector whose reflection band can be tuned across part of the electromagnetic spectrum by an appropriate choice of its helical pitch. Said pitch noteworthy depends on the ratio of nematic precursor material to chiral inducer compound in the liquid crystal precursor, and on the temperature of polymerization. After polymerization, the helical pitch, and hence the reflection color of the material, remains fixed.

As known to the skilled person, low amounts of chiral inducer result in a low helical twisting and hence in a large helical pitch. Therefore, low amounts of the chiral inducer generate a reflection band of the resulting polymer at the long wavelength end of the spectrum, typically in the infrared or red region, whereas higher amounts of inducer generate a reflection band of the resulting polymer at the short wavelength end of the spectrum, typically in the blue or UV region.

Attention must also be paid to the handedness of the chiral inducer, i.e. whether a determined inducer results in a left or in a right helical pitch, resulting in respective opposite circular polarization of the reflected light. Isomannide derivatives are known to induce the reflection of left circular polarized light, whereas isosorbide derivatives are known to induce the reflection of right circular polarized light.

Hereafter is given a typical example of a cholesteric liquid crystal polymer precursor composition, which can be applied by the continuous ink-jet printing process:

Example 1

| Composition | Weight % |
| --- | --- |
| Acetone | 52.25 |
| 2-methyl-1,4-phenylene bis(4-(4-(acryloyloxy)butoxy)benzoate) | 38.8 |
| (3R,3aR,6R,6aR)-hexahydrofuro[3,2-b]furan-3,6-diyl bis(4-(4-(acryloyloxy)benzoyloxy)-3-methoxybenzoate) | 7.5 |
| Irgacure 907 | 1.0 |
| LiClO4 | 0.45 |

Example 2

| Composition | Weight % |
| --- | --- |
| Acetone | 52.25 |
| 2-methyl-1,4-phenylene bis(4-(4-(acryloyloxy)butoxy)benzoate) | 38.8 |
| (3R,3aR,6R,6aR)-6-(4-(4-(acryloyloxy)-3-methoxybenzoyloxy)-3-methoxybenzoyloxy)hexahydrofuro[3,2-b]furan-3-yl 4-(4-(acryloyloxy)benzoyloxy)-3-methoxybenzoate | 7.5 |
| Irgacure 907 | 1.0 |
| LiClO4 | 0.45 |

Example 3

| Composition | Weight % |
| --- | --- |
| Acetone | 55.29 |
| 2-methyl-1,4-phenylene bis(4-(4-(acryloyloxy)butoxy)benzoate) | 41.07 |
| (3R,3aR,6S,6aR)-hexahydrofuro[3,2-b]furan-3,6-diyl bis(4-(4-(acryloyloxy)benzoyloxy)-3-methoxybenzoate) | 2.11 |
| Irgacure 907 | 1.05 |
| LiClO4 | 0.48 |

Example 4

| Composition | Weight % |
| --- | --- |
| Acetone | 52.25 |
| 2-methyl-1,4-phenylene bis(4-(4-(acryloyloxy)butoxy)benzoate) | 38.8 |
| (3R,3aR,6R,6aR)-hexahydrofuro[3,2-b]furan-3,6-diyl bis(4-(4-(acryloyloxy)-3-methoxybenzoyloxy)-3-methoxybenzoate) | 7.5 |
| Irgacure 907 | 1.0 |
| LiClO4 | 0.45 |

Example 5

| Composition | Weight % |
| --- | --- |
| Acetone | 52.25 |
| 2-methyl-1,4-phenylene bis(4-(4-(acryloyloxy)butoxy)benzoate) | 38.8 |
| (3R,3aR,6R,6aR)-hexahydrofuro[3,2-b]furan-3,6-diyl bis(4-(4-(acryloyloxy)benzoyloxy)-3-methoxybenzoate) | 7.5 |
| Irgacure 907 | 1.0 |
| LiClO4 | 0.45 |

Example 6

| Composition | Weight % |
| --- | --- |
| Methyl ethyl ketone (MEK) | 52.25 |
| 2-methyl-1,4-phenylene bis(4-(4-(acryloyloxy)butoxy)benzoate) | 38.8 |
| (3R,3aR,6R,6aR)-hexahydrofuro[3,2-b]furan-3,6-diyl bis(4-(4-(acryloyloxy)benzoyloxy)benzoate) | 7.5 |
| Irgacure 907 | 1.0 |
| LiClO4 | 0.45 |

Example 7

| Composition | Weight % |
| --- | --- |
| Acetone | 48.6 |
| 2-methyl-1,4-phenylene bis(4-(4-(acryloyloxy)butoxy)benzoate) | 36.1 |
| (3R,3aR,6R,6aR)-hexahydrofuro[3,2-b]furan-3,6-diyl bis(4-(4-(acryloyloxy)butoxy)benzoate) | 13.95 |
| Irgacure 907 | 0.93 |
| LiClO4 | 0.42 |

Example 8

| Composition | Weight % |
| --- | --- |
| Acetone | 49.25 |
| 2-methyl-1,4-phenylene bis(4-(4-(acryloyloxy)butoxy)benzoate) | 36.6 |
| (3R,3aR,6R,6aR)-hexahydrofuro[3,2-b]furan-3,6-diyl bis(4-(acryloyloxy)-2-methylbenzoate) | 12.74 |
| Irgacure 907 | 0.94 |
| LiClO4 | 0.47 |

Based on the indications and exemplary embodiments given hereinbefore, the skilled person is enabled to derive further embodiments of the present invention.

What is claimed is:

1. A composition comprising a monomeric or oligomeric precursor of a liquid crystal polymer, a chiral dopant, and at least one of an inorganic luminescent compound, an organic luminescent compound, an IR-absorber, a magnetic material, and a forensic marker, and wherein the monomeric or oligomeric precursor of a liquid crystal polymer comprises a bisacrylate, and the chiral dopant comprises at least one of:

a chiral dopant according to formula (I)

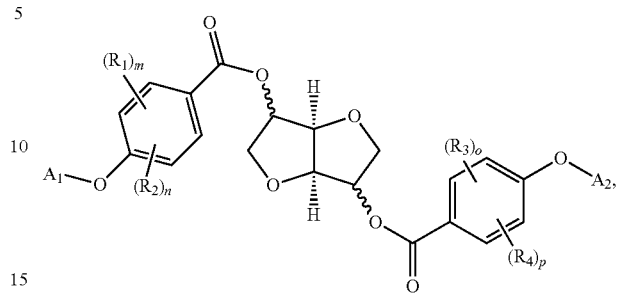

a chiral dopant according to formula (IA):

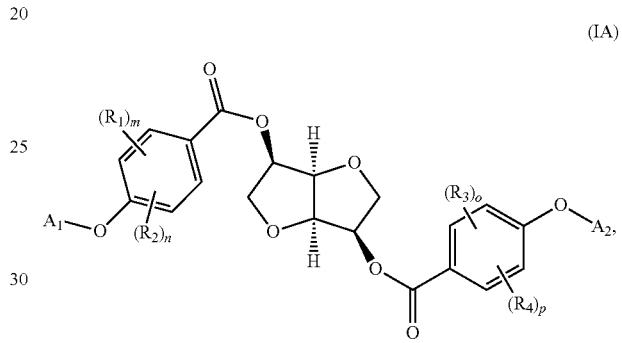

a chiral dopant represented by the formula (IB)

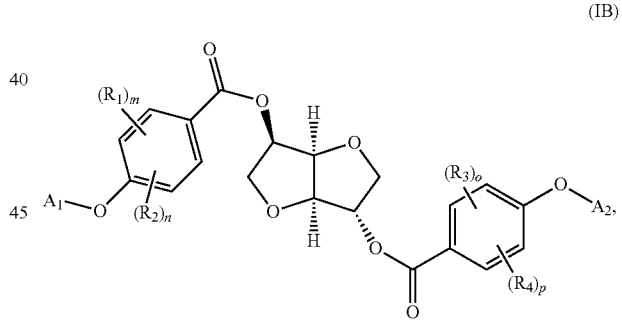

wherein
$A_1$ and $A_2$ denote each independently a group:
i) —[(CH$_2$)y-O]z-C(O)—CH=CH$_2$;
ii) —C(O)-D$_1$-O—[(CH$_2$)y-O]z-C(O)—CH=CH$_2$;
iii) —C(O)-D$_2$-O—[(CH$_2$)y-O]z-C(O)—CH=CH$_2$;
D$_1$ denotes a group

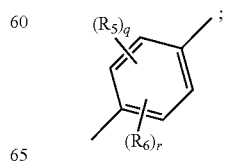

D₂ denotes a group

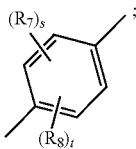

$R_1, R_2, R_3, R_4, R_5, R_6, R_7$ and $R_8$ denote each independently $C_1$-$C_6$ alkyl or $C_1$-$C_6$ alkoxy;
m, n, o, p, q, r, s, and t denote each independently 0, 1, 2;
y denotes 0, 1,2,3,4,5,6;
z equal 0 if y equal 0 and z equal 1 if y equal 1 to 6.

2. The composition according to claim 1 wherein $R_1$, $R_2$, $R_3$, $R_4$, $R_5$, $R_6$, $R_7$ and $R_8$ denote each independently $C_1$-$C_6$ alkyl.

3. The composition according to claim 1 wherein $R_1$, $R_2$, $R_3$, $R_4$, $R_5$, $R_6$, $R_7$ and $R_8$ denote each independently $C_1$-$C_6$ alkoxy.

4. The composition according to claim 1 wherein $A_1$ and $A_2$ denote each independently
i) —[(CH₂)y-O]z-C(O)—CH=CH₂.

5. The composition according to claim 1 wherein $A_1$ and $A_2$ denote each independently
ii) —C(O)-D₁-O—[(CH₂)y-O]z-C(O)—CH=CH₂;
iii) —C(O)-D₂-O—[(CH₂)y-O]z-C(O)—CH=CH₂.

6. The composition according to claim 1 wherein the alkyl or alkoxy group of $R_1, R_2, R_3, R_4, R_5, R_6, R_7$ and $R_8$ comprise 4 or 6 carbon atoms.

7. The composition according to claim 1 wherein the chiral dopant comprises at least one of:
(3R,3aR,6R,6aR)-hexahydrofuro[3,2-b]furan-3,6-diylbis (4-(4-(acryloyloxy)benzoyloxy)benzoate);
(3R,3aR,6R,6aR)-hexahydrofuro[3,2-b]furan-3,6-diylbis (4-(4-(acryloyloxy)butoxy)benzoate);
(3R,3aR,6R,6aR)-hexahydrofuro[3,2-b]furan-3,6-diylbis (4-(acryloyloxy)-2-methylbenzoate);
(3R,3aR,6R,6aR)-hexahydrofuro[3,2-b]furan-3,6-diylbis (4-(4-(acryloyloxy)benzoyloxy)-3-methoxybenzoate);
(3R,3aR,6R,6aR)-hexahydrofuro[3,2-b]furan-3,6-diylbis (4-(4-(acryloyloxy)-3-methoxybenzoyloxy)benzoate);
(3R,3aR,6R,6aR)-6-(4-(4-(acryloyloxy)-3-methoxybenzoyloxy)-3-methoxybenzoyloxy)hexahydro furo[3,2-b]furan-3-yl-4-(4-(acryloyloxy)benzoyloxy)-3-methoxybenzoate;
(3R,3aR,6R,6aR)-hexahydrofuro[3,2-b]furan-3,6-diylbis (4-(4-(acryloyloxy)-3-methoxybenzoyloxy)-3-methoxybenzoate); and
(3R,3aR,6R,6aR)-hexahydrofuro[3,2-b]furan-3,6-diylbis (4-(4-(acryloyloxy)benzoyloxy)-3-methoxybenzoate).

8. The composition according to claim 1 wherein the monomeric or oligomeric precursor of a liquid crystal polymer comprises at least one of 2-methyl-1,4-phenylene bis(4-(4-(acryloyloxy)butoxy)benzoate; 1,4-phenylene bis(4-(4-(acryloyloxy)butoxy)benzoate); 2-methyl-1,4-phenylene bis (4-(6-(acryloyloxy)hexyloxy)benzoate); 1,4-phenylene bis (4-((4-(acryloyloxy)butoxy)carbonyloxy)benzoate); and 2-methyl-1,4-phenylene bis(4-((4-(acryloyloxy)butoxy) carbonyloxy)benzoate).

9. The composition according to claim 1 further comprising a solvent.

10. The composition according to claim 9 wherein the composition is an ink-jet printing composition.

11. The composition according to claim 10 wherein the composition has a viscosity in a range of 4 to 30 mPa·s at 25° C.

12. The composition according to claim 9 wherein the solvent comprises methyl-ethyl-ketone, acetone, ethylacetate, ethyl 3-ethoxypropionate or toluene.

13. The composition according to claim 10 wherein the solvent is present in a range of 10% to 95% by weight of the composition.

14. The composition according to claim 13 wherein the solvent is present in a range of 45% to 85% by weight of the composition.

15. The composition according to claim 10 further comprising a dissolved conducting agent.

16. The composition according to claim 15 wherein the dissolved conducting agent comprises dissolved lithium nitrate, lithium perchlorate, tetrabutylammonium chloride or tetrabutylammonium tetrafluoroborate.

17. The composition according to claim 15 wherein the dissolved conducting agent is present in a concentration range of 0.1 to 5% by weight of the composition.

18. The composition according to claim 1 wherein the at least one of an inorganic luminescent compound, an organic luminescent compound, an IR-absorber, a magnetic material, and a forensic marker comprises an inorganic luminescent compound or an organic luminescent compound.

19. The composition according to claim 18 wherein the inorganic luminescent compound or the organic luminescent compound is present in a range of 0.01% to 5% by weight of the composition.

20. The composition according to claim 18 further comprising an IR-absorber.

21. The composition according to claim 20 wherein the IR-absorber is present in a range of 0.1% to 10% by weight of the composition.

22. The composition according to claim 18 further comprising a magnetic material.

23. The composition according to claim 12 wherein the magnetic material is present in a range of 0.1% to 10% by weight of the composition.

24. The composition according to claim 1 wherein the composition further comprises an organic solvent, and a photoinitiator.

25. The composition according to claim 24 wherein the at least one photoinitiator is present in a range of 0.5% to 5% by weight of the composition.

26. The composition according to claim 24 wherein the composition is formulated to be applied by ink-jet printing.

27. The composition according to claim 24 wherein the at least one of an inorganic luminescent compound, an organic luminescent compound, an IR-absorber, a magnetic material, and a forensic marker comprises an inorganic luminescent compound or an organic luminescent compound.

28. The composition according to claim 27, further comprising a magnetic material.

29. The composition according to claim 27, further comprising an IR-absorber.

30. The composition according to claim 27 further including a stabilizer.

31. The composition according to claim 27 further including a silane derivative.

* * * * *

UNITED STATES PATENT AND TRADEMARK OFFICE
CERTIFICATE OF CORRECTION

PATENT NO. : 8,734,678 B2  
APPLICATION NO. : 13/532240  
DATED : May 27, 2014  
INVENTOR(S) : Marguerettaz et al.

Page 1 of 1

It is certified that error appears in the above-identified patent and that said Letters Patent is hereby corrected as shown below:

In the Claims

Column 23, Claim 7, lines 35, 37, 39, 41, 43, 49, and 52 delete "diylbis" and insert --diyl bis--.

Signed and Sealed this  
Twenty-third Day of December, 2014

Michelle K. Lee  
*Deputy Director of the United States Patent and Trademark Office*